United States Patent [19]

Sanderson et al.

[11] Patent Number: 5,243,100
[45] Date of Patent: Sep. 7, 1993

[54] PREPARATION OF TERTIARY BUTYL ALCOHOL USING PROMOTED CYCLOALKENYL IRON CATALYST

[75] Inventors: John R. Sanderson, Leander; John F. Knifton, Austin, both of Tex.

[73] Assignee: Texaco Chemical Company, White Plains, N.Y.

[21] Appl. No.: 941,506

[22] Filed: Sep. 8, 1992

[51] Int. Cl.$^5$ ............... C07C 29/00; C07C 29/132; C07C 31/12
[52] U.S. Cl. .................. 568/909.8; 568/922
[58] Field of Search ......................... 568/909.8

[56] References Cited

U.S. PATENT DOCUMENTS

| | | | |
|---|---|---|---|
| 4,006,194 | 2/1977 | Luberoff et al. | 568/909.8 |
| 4,910,349 | 3/1990 | Sanderson et al. | 568/909.8 |
| 4,912,266 | 3/1990 | Sanderson et al. | 568/909.8 |
| 4,922,034 | 5/1990 | Sanderson et al. | 568/909.8 |
| 4,922,035 | 5/1990 | Sanderson et al. | 568/909.8 |
| 4,922,036 | 5/1990 | Sanderson et al. | 568/909.8 |
| 4,970,346 | 11/1990 | Sanderson et al. | 568/909.8 |
| 4,978,799 | 12/1990 | Sanderson et al. | 568/909.8 |
| 4,992,602 | 2/1991 | Sanderson et al. | 568/909.8 |
| 5,025,113 | 6/1991 | Sanderson et al. | 568/909.8 |
| 5,120,886 | 6/1992 | Lyons et al. | 568/909.8 |

*Primary Examiner*—Joseph E. Evans
*Attorney, Agent, or Firm*—Jack H. Park; Kenneth R. Priem; Carl G. Ries

[57] ABSTRACT

A method for preparing tertiary butyl alcohol wherein a solution of a tertiary butyl hydroperoxide feedstock comprising a solution of tertiary butyl hydroperoxide in tertiary butyl alcohol is charged to a hydroperoxide decomposition reaction zone containing a catalytically effective amount of a hydroperoxide decomposition catalyst consisting essentially of a mixture of a soluble cycloalkenyl iron compound with a soluble ruthenium compound, and is brought into contact with the catalyst in liquid phase with agitation under hydroperoxide decomposition reaction conditions to convert the tertiary butyl hydroperoxide to decomposition products, principally tertiary butyl alcohol.

10 Claims, No Drawings

PREPARATION OF TERTIARY BUTYL ALCOHOL USING PROMOTED CYCLOALKENYL IRON CATALYST

BACKGROUND OF THE INVENTION

1. Field of the Invention

This invention relates to the catalytic decomposition of tertiary butyl hydroperoxide (THHP). More particularly, this invention relates to a method for the preparation of tertiary butyl alcohol (TBA) by the catalytic decomposition of tertiary butyl hydroperoxide. Still more particularly, this invention relates to a method wherein a soluble cycloalkenyl iron compound promoted with a soluble ruthenium co-catalyst is used to catalyze the decomposition of tertiary butyl hydroperoxide to tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

In the text entitled "Organic Peroxides" edited by Daniel Swern (Wiley Interscience, a Division of John Wiley & Sons, New York), in Vol. II on page 157 it is stated that the metal-ion-catalyzed decomposition of primary hydroperoxides yields mainly alcohols, aldehydes and carboxylic acids, citing as an example the decomposition of hydroxymethyl hydroperoxide with aqueous ferrous sulfate to provide formaldehyde, formic acid and water.

Quin U.S. Pat. No. 2,854,487 discloses the hydrogenation of hydrocarbon peroxides in the presence of hydrogen and palladium on activated alumina to provide carbinols.

In Massie U.S. Pat. No. 3,775,472 a process is disclosed wherein alkyl substituted aromatic hydrocarbons are oxidized to products such as aromatic alcohols, aldehydes and carboxylic acids in the presence of ruthenium compounds.

Grane U.S. Pat. No. 3,474,151 discloses that tertiary butyl alcohol starts to dehydrate at 450° F. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decompose by "hot aging" at 250°–350° F. at a pressure lower than the pressure in the oxidation zone. The tertiary butyl alcohol can be further subjected to a clean-up treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

BACKGROUND INFORMATION

In U.S. Pat. No. 3,505,360, Allison et al. disclose a method wherein an alkenyl hydroperoxide is decomposed in the presence of a catalyst based on a compound of a Group IV-A, V-A or VI-A metal. Taylor et al., in U.S. Pat. No. 4,508,923 disclose the use of a catalyst system comprising ruthenium and chromium for decomposing organic hydroperoxides. The use of a cobalt borate catalyst for the decomposition of hydroperoxides is disclosed in Sanderson et al. U.S. Pat. No. 4,547,598.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Sanderson et al. disclose the use of a variety of catalysts for the decomposition of tertiary butyl hydroperoxide in a series of U.S. patents, including a catalyst composed of unsupported nickel, copper, chromia and iron (U.S. Pat. No. 4,704,482), a catalyst composed of iron, copper, chromia and cobalt (U.S. Pat. No. 4,705,903), a catalyst composed of a base treated hydrogenation catalyst from groups VIB or VIIIB of the Periodic Table (U.S. Pat. No. 4,742,179), a catalyst consisting essentially of nickel, copper, chromium and barium (U.S. Pat. No. 4,873,380), a catalyst composed of a metal phthalocyanine promoted with a rhenium compound (U.S. Pat. No. 4,910,349), a catalyst composed of a base promoted metal phthalocyanine compound (U.S. Pat. No. 4,912,269), a catalyst composed of a soluble ruthenium compound promoted with a bidentate ligand (U.S. Pat. No. 4,912,033), a catalyst composed of a metal porphine such as iron (III) or manganese (III) promoted with an alkyl thiol or an amine, a catalyst composed of an imidazole promoted metal phthalocyanine compound (U.S. Pat. No. 4,912,266), (U.S. Pat. No. 4,922,034), or a catalyst composed of a metal phthalocyanine promoted with a thiol and a free radical inhibitor (U.S. Pat. No. 4,922,035), a catalyst composed of a borate promoted metal phthalocyanine (U.S. Pat. No. 4,922,036).

Sanderson et al. also disclose that a catalyst composed of a soluble ruthenium compound and an iron compound such as a ferrous or ferric salt of an organic carboxylic acid (e.g., an acetate, a borate, a bromide, a chloride, a 1,3-propanedionate, a 2-ethylhexanoate, an iodide, a nitrate, a 2,4-pentanedionate, a perchlorate or a sulfate) in their U.S. Pat. No. 5,025,113.

When isobutane is reacted with molecular oxygen, the principal products of the reaction are tertiary butyl alcohol and tertiary butyl hydroperoxide. However, minor amounts of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

A listing of the components present in a representative reaction product, and their nominal boiling points (NBP) is given in Table A.

TABLE A

| Component | NBP (°C.) |
| --- | --- |
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl peroxide but tends to distill overhead, which suggests that it forms a minimum boiling azeotrope with another component or components.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

A feedstock for the present invention is suitably one formed by the oxidation of isobutane with molecular oxygen to provide an oxidation reaction product containing a solution of tertiary butyl hydroperoxide and tertiary butyl alcohol in unreacted isobutane. The feedstock for the present invention may comprise tertiary butyl hydroperoxide dissolved in tertiary butyl alcohol and is recovered from the isobutane oxidation reaction product by distillation. The feedstock is charged to a catalytic decomposition zone wherein the tertiary butyl hydroperoxide is decomposed in the presence of a soluble cycloalkenyl iron compound to provide a decomposition reaction product characterized by a high conversion rate and a high selectivity of tertiary butyl hydroperoxide to tertiary butyl alcohol.

The tertiary butyl alcohol will not be the only decomposition product that is formed. Minor amounts of other oxygen-containing materials such as those listed above will also be formed.

The tertiary butyl alcohol that is recovered from the decomposition reaction mixture will be contaminated with the oxygenated impurities.

DESCRIPTION OF THE PROCESS OF THE PRESENT INVENTION

The starting materials for the process of the present invention are a tertiary butyl hydroperoxide feedstock and a catalyst system composed of a soluble cycloalkenyl iron compound promoted with a soluble ruthenium compound.

The Tertiary Butyl Hydroperoxide Feedstock

The feedstock to be used in accordance with the present invention is a tertiary butyl alcohol solution of tertiary butyl hydroperoxide that preferably contains from about 5 to about 30 wt. % of tertiary butyl hydroperoxide. As indicated, the feedstock is suitably prepared by the oxidation of isobutane to form an oxidation product from which a feedstock of the present invention can be recovered by distillation.

The Catalyst System

The catalyst system to be used in accordance with the present invention is a hydroperoxide decomposition catalyst consisting essentially of a soluble cycloalkenyl iron compound promoted with a soluble ruthenium compound.

The soluble cycloalkenyl iron compound may suitably consist essentially of an alkylcycloalkadienyl iron compound or a cycloalkenyl iron carbonyl.

Soluble alkylcycloalkadienyl iron compounds include compounds such as bis(pentamethylcyclopentadienyl) iron, a compound having the formula:

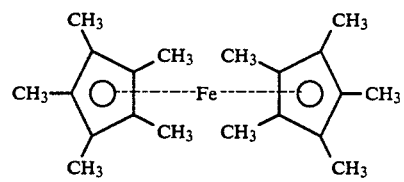

Soluble cycloalkenyl iron carbonyl compounds include dimers such as cyclopentadienyl iron dicarbonyl dimer having the formula:

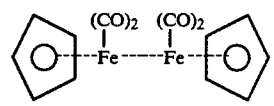

Also included cylcoalkenyl iron tricarbonyls such as cyclohexadiene iron tricarbonyl and cyclooctatetraene iron tricarbonyl. The formula for cyclohexadiene iron tricarbonyl is:

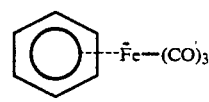

The formula for cyclooctatetraene iron tricarbonyl is:

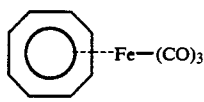

The Soluble Ruthenium Compound

The soluble ruthenium compounds to be used in accordance with the present invention are selected from the group consisting of ruthenium salts of mineral acids and organic carboxylic acids. For example, the ruthenium compound may be a salt of a mineral acid, such as ruthenium (III) chloride hydrate, ruthenium (III) bromide, ruthenium (III) iodide, tricarbonylruthenium nitrate, or as a salt of a suitable organic carboxylic acid such as, for example, ruthenium (III) acetate, ruthenium naphthenate, ruthenium valerate and ruthenium complexes with carbonyl-containing ligands such as ruthenium(III) acetylacetonate.

Additional examples of ruthenium compounds include ruthenium octonate, ruthenium laurate, ruthenium stearate, ruthenium linoleate, ruthenium nitrate, triruthenium dodecacarbonyl (i.e., dodecacarbonyl), ruthenium sulfate and ruthenium pentacarbonyl.

From about 0.01 to about 10 parts by weight of soluble ruthenium compound should be employed per part of soluble cycloalkenyl iron compound, e.g., from about 0.1 to about 3 parts by weight of soluble ruthenium compound per part by weight of soluble iron compound and more preferably from about 0.1 to about 2 parts by weight of soluble ruthenium compound per part by weight of soluble iron compound.

Stated differently, the combination of the soluble cycloalkenyl iron compound with the soluble ruthenium compound may be utilized in the weight ratio of iron to ruthenium of 0.01:1 to 100:1. Preferably, the iron/ruthenium weight ratio is in the range of about 1:1 to about 10:1.

Stated in a still different manner, the concentration of iron in the tertiary butyl hydroperoxide feedstock may vary widely, constituting for example, about 0.001 to about 5 wt. % of the weight of the tertiary butyl hydroperoxide feedstock and the ruthenium compound may be present in the ratio of about 0.1 to about 3 parts by weight of soluble ruthenium compound per part of soluble cycloalkenyl iron compound. In general, the catalyst system of the present invention may be advantageously present in the tertiary butyl hydroperoxide feedstock in an amount, based on the iron compound, of about 0.01 to about 5,000 ppm of soluble cycloalkenyl iron compound and the ruthenium compound may be present in the ratio of about 0.1 to about 3 parts by weight of soluble ruthenium compound per part of soluble cycloalkenyl iron compound.

Catalytic Decomposition of Tertiary Butyl Hydroperoxide

The process of the present invention may be conducted batchwise in kettles or by continuously passing the reactants through a tubular reactor.

The catalytic decomposition of the tertiary butyl hydroperoxide is preferably conducted at a temperature within the range of about 25° to about 250° C. and, more preferably, at a temperature within the range of about 40° to about 150° C. The reaction is preferably conducted at autogenous pressure although superatmospheric pressures up to about 1000 psig. may be used, if desired.

Flow rates of the charge solution to the reaction zone should be adjusted in order to provide an appropriate contact time within the reactor. In a batch process, the holding time may suitably be from about 0.5 to about 10 hours, and more preferably about 1 to 3 hours.

In accordance with the most preferred embodiment of the present invention, isobutane is reacted with oxygen in an oxidation zone under oxidation reaction conditions including a temperature of about 135° to about 155° C., a pressure of about 300 to about 800 psig., and a holding time of about 2 to about 6 hours to provide an initial oxidation reaction product comprising unreacted isobutane, tertiary butyl hydroperoxide, tertiary butyl alcohol, and oxygen-containing by-products. The oxidation reaction product is fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt. % of tertiary butyl hydroperoxide. If the tertiary butyl hydroperoxide concentration is excessive, additional tertiary butyl alcohol may be added.

The tertiary butyl alcohol solution of tertiary butyl hydroperoxide is then charged to a catalytic hydroperoxide decomposition zone where it is brought into contact with a co-catalyst consisting essentially of a cycloalkenyl iron compound and the soluble ruthenium compound to convert the tertiary butyl hydroperoxide to tertiary butyl alcohol with high yields and selectivities.

The reaction product from the tertiary butyl hydroperoxide decomposition step may then be fractionated in any suitable manner, such as by extractive distillation to recover the tertiary butyl alcohol.

SPECIFIC EXAMPLES

The invention will be further illustrated by the following specific examples which are given by way of illustration and not as limitations on the scope of this invention.

Procedure

A 20 wt. % solution of TBHP in TBA and catalyst were charged to an autoclave equipped with glass liner, Magnedrive stirrer, cooling coil, and electric heater. The mixture was heated to the desired temperature for the desired time with vigorous stirring. The mixture was then cooled to ambient temperature, filtered if any solid residue present, and analyzed by GC. The results are defined in the attached tables.

TABLE I

CATALYTIC CONVERSION OF TERT-BUTYL HYDROPEROXIDE TO TERT-BUTYL ALCOHOL

| Notebook Number | 6844-10-G | 6952-43 | 6952-45 | 6952-46 |
|---|---|---|---|---|
| Catalyst | | bis(pentamethylcyclopentadienyl) Iron Ruthenium Acetylacetonate (.02 g) | | |
| Solution (g) | | 100.0 | 100.0 | 100.0 |
| Catalyst (g) | | 0.10 | 0.10 | 0.10 |
| Catalyst (%) | | 0.1 | 0.1 | 0.1 |
| Temperature (°C.) | | 80 | 120 | 140 |
| Reaction Time (hr) | | 4 | 4 | 4 |
| TBHP Conversion | | 99.1 | 99.9 | 100.0 |

TABLE I-continued

CATALYTIC CONVERSION OF TERT-BUTYL HYDROPEROXIDE TO TERT-BUTYL ALCOHOL

| Notebook Number | 6844-10-G | 6952-43 | 6952-45 | 6952-46 |
|---|---|---|---|---|
| Selectivity IC4= (mol. %) |  | 0.0 | 0.1 | 0.0 |
| Sel. Acetone (mol. %) |  | 9.1 | 16.1 | 19.5 |
| Sel. Methanol (mol. %) |  | 1.6 | 5.0 | 7.7 |
| Sel. TBA (mol. %) |  | 85.0 | 80.8 | 81.0 |
| Sel. DTBP (mol. %) |  | 5.9 | 3.1 | −0.5 |
| Remarks | H2O Free Basis | H2O Free Basis | H2O Free Basis | H2O Free Basis |
| Composition |  |  |  |  |
| IC4= | 0.000 | 0.000 | 0.011 | 0.004 |
| MEOH/MF | 0.020 | 0.127 | 0.360 | 0.542 |
| Acetone | 0.037 | 1.148 | 2.013 | 2.434 |
| TBA | 79.823 | 95.480 | 95.548 | 95.560 |
| DTBP | 0.145 | 1.049 | 0.625 | 0.066 |
| TBHP | 19.090 | 0.167 | 0.010 | 0.009 |

TABLE O

CATALYTIC CONVERSION OF TERT-BUTYL HYDROPEROXIDE TO TERT-BUTYL ALCOHOL

| Notebook Number | 6844-10-G | 6952-12 | 6952-13 | 6952-14 | 6952-15 |
|---|---|---|---|---|---|
| Catalyst | bispentamethylcyclopentadienyl) Iron | | | | |
| Solution (g) |  | 100.0 | 100.0 | 100.0 | 100.0 |
| Catalyst (g) |  | 0.10 | 0.10 | 0.10 | 0.10 |
| Catalyst (%) |  | 0.1 | 0.1 | 0.1 | 0.1 |
| Temperature (°C.) |  | 80 | 100 | 120 | 140 |
| Reaction Time (hr) |  | 4 | 4 | 4 | 4 |
| TBHP Conversion (mol. %) |  | 0.0 | 32.9 | 93.4 | 99.9 |
| Selectivity IC4= (mol. %) |  | 0.0 | 0.0 | 0.0 | 0.0 |
| Sel. Acetone (mol. %) |  | 0.0 | 11.0 | 16.5 | 25.1 |
| Sel. Methanol (mol. %) |  | 0.0 | 2.9 | 7.2 | 11.7 |
| Sel. TBA (mol. %) |  | 0.0 | 86.8 | 82.5 | 75.7 |
| Sel. DTBP (mol. %) |  | 0.0 | 2.2 | 1.0 | −0.7 |
| Remarks | H2O Free Basis | H2O Free Basis | H2O Free Basis | H2O Free Basis | H2O Free Basis |
| Composition |  |  |  |  |  |
| IC4= | 0.000 | 0.000 | 0.001 | 0.002 | 0.003 |
| MEOH/MF | 0.020 | 0.018 | 0.084 | 0.476 | 0.814 |
| Acetone | 0.037 | 0.165 | 0.483 | 1.930 | 3.117 |
| TBA | 79.823 | 78.772 | 84.837 | 94.953 | 95.040 |
| DTBP | 0.145 | 0.139 | 0.255 | 0.296 | 0.031 |
| TBHP | 19.090 | 19.631 | 12.817 | 1.255 | 0.015 |

TABLE II

CATALYTIC CONVERSION OF TERT-BUTYL HYDROPEROXIDE TO TERT-BUTYL ALCOHOL

| Notebook Number | 6844-10-G | 6952-47 | 6952-48 | 6952-49 | 6952-50 |
|---|---|---|---|---|---|
| Catalyst | bis(Pentamethylcyclopentadienyl) Iron Copper Acetylacetonate (.02 g) | | | | |
| Solution (g) |  | 100.0 | 100.0 | 100.0 | 100.0 |
| Catalyst (g) |  | 0.10 | 0.10 | 0.10 | 0.10 |
| Catalyst (%) |  | 0.1 | 0.1 | 0.1 | 0.1 |
| Temperature (°C.) |  | 80 | 100 | 120 | 140 |
| Reaction Time (hr) |  | 4 | 4 | 4 | 4 |
| TBHP Conversion (mol. %) |  | 42.9 | 85.0 | 97.9 | 99.9 |
| Selectivity IC4= (mol. %) |  | 0.0 | 0.0 | 0.1 | 0.2 |
| Sel. Acetone (mol. %) |  | 11.2 | 15.0 | 24.7 | 29.8 |
| Sel. Methanol (mol. %) |  | 2.0 | 4.4 | 9.4 | 11.7 |
| Sel. TBA (mol. %) |  | 83.1 | 81.8 | 73.9 | 70.8 |
| Sel. DTBP (mol. %) |  | 5.7 | 3.2 | 1.4 | −0.6 |
| Remarks | H2O Free Basis | H2O Free Basis | H2O Free Basis | H2O Free Basis | H2O Free Basis |
| Composition |  |  |  |  |  |
| IC4= | 0.000 | 0.001 | 0.001 | 0.006 | 0.028 |
| MEOH/MF | 0.020 | 0.079 | 0.274 | 0.643 | 0.812 |
| Acetone | 0.037 | 0.625 | 1.605 | 3.011 | 3.699 |
| TBA | 79.823 | 86.397 | 92.797 | 94.479 | 94.237 |
| DTBP | 0.145 | 0.526 | 0.571 | 0.356 | 0.053 |
| TBHP | 19.090 | 10.909 | 2.870 | 0.404 | 0.011 |

TABLE III

CATALYTIC CONVERSION OF TERT-BUTYL HYDROPEROXIDE TO TERT-BUTYL ALCOHOL

| Notebook Number | 6844-10-G | 6952-51 | 6952-52 | 6952-53 | 6952-54 |
|---|---|---|---|---|---|
| Catalyst | Cyclooctatetraene Iron Tricarbonyl | | | | |

TABLE III-continued
CATALYTIC CONVERSION OF TERT-BUTYL HYDROPEROXIDE TO TERT-BUTYL ALCOHOL

| Notebook Number | 6844-10-G | 6952-51 | 6952-52 | 6952-53 | 6952-54 |
|---|---|---|---|---|---|
| | | Copper Acetylacetonate (.02 g) | | | |
| Solution (g) | | 100.0 | 100.0 | 100.0 | 100.0 |
| Catalyst (g) | | 0.10 | 0.10 | 0.10 | 0.10 |
| Catalyst (%) | | 0.1 | 0.1 | 0.1 | 0.1 |
| Temperature (°C.) | | 80 | 100 | 120 | 140 |
| Reaction Time (hr) | | 4 | 4 | 4 | 4 |
| TBHP Conversion (mol. %) | | 98.6 | 99.8 | 99.9 | 100.0 |
| Selectivity IC4= (mol. %) | | 0.0 | 0.2 | 0.4 | 1.1 |
| Sel. Acetone (mol. %) | | 7.7 | 14.5 | 20.2 | 27.5 |
| Sel. Methanol (mol. %) | | 2.6 | 4.7 | 7.0 | 9.4 |
| Sel. TBA (mol. %) | | 88.1 | 82.1 | 77.7 | 73.0 |
| Sel. DTBP (mol. %) | | 4.2 | 3.3 | 2.1 | −0.5 |
| Remarks | H2O Free Basis | H2O Free Basis | H2O Free Basis | H2O Free Basis | H2O Free Basis |
| Composition | | | | | |
| IC4= | 0.000 | 0.002 | 0.026 | 0.051 | 0.126 |
| MEOH/MF | 0.020 | 0.197 | 0.339 | 0.498 | 0.657 |
| Acetone | 0.037 | 0.973 | 1.823 | 2.517 | 3.422 |
| TBA | 79.823 | 95.681 | 95.469 | 94.917 | 94.062 |
| DTBP | 0.145 | 0.782 | 0.659 | 0.477 | 0.061 |
| TBHP | 19.090 | 0.271 | 0.035 | 0.011 | 0.000 |

Discussion

The combination of bis(pentamethylcyclopentadienyl) iron and ruthenium acetylacetonate is a very active catalyst system for the conversion of TBHP to TBA. For example, at 80° C. and a 4.0 hour reaction time, the iron/ruthenium combination gave 99.1% TBHP conversion and a selectivity to TBA of 85.0%. Under the same conditions, bis(pentamethylcyclopentadienyl) iron alone gave no conversion of TBHP to TBA. (See Table I and Table O).

In addition, the Fe/Ru combination gave an 81.0% selectivity to TBA even at 140° C. The Fe catalyst alone gave 75.7% selectivity at 140°.

The Fe/Ru couple is also more active than a bis(pentamethylcyclopentadienyl) iron and a copper acetylacetonate couple. (Compare Table I with Table II and III.) At 80° C., the Fe/Cu couple gave 42.9% conversion—better than the Fe catalyst alone (Table O), but still poorer results than the Fe/Ru couple.

Having thus described our invention, what is claimed is:

1. In a method wherein a solution of a tertiary butyl hydroperoxide charge stock in tertiary butyl alcohol is brought into contact with a catalytically effective amount of a hydroperoxide decomposition catalyst in a hydroperoxide decomposition reaction zone in liquid phase with agitation to convert said tertiary butyl hydroperoxide to decomposition products, principally tertiary butyl alcohol, the improvement which comprises:
   a) using, as said hydroperoxide decomposition catalyst, a soluble iron hydroperoxide decomposition catalyst consisting essentially of a co-catalyst mixture of a soluble cycloalkenyl iron compound with a soluble ruthenium compound, and
   b) recovering tertiary butyl alcohol from the products of said hydroperoxide decomposition reaction.

2. A method as in claim 1 wherein the soluble alkenyl iron compound is selected from the group consisting of alkylcycloalkadienyl iron compounds and cycloalkenyl iron carbonyls and the ruthenium compound consists essentially of a ruthenium salt of a mineral acid or an organic carboxylic acid.

3. A method as in claim 2 wherein the soluble iron compound is a bis(alkylcycloalkadienyl) iron compound and the soluble ruthenium compound is a salt of an organic carboxylic acid.

4. A method as in claim 3 wherein the soluble bis(alkylcycloalkadienyl) iron compound is bis(pentamethylcyclopentadienyl) iron and the soluble ruthenium compound is ruthenium acetylacetonate.

5. A method as in claim 2 wherein the soluble iron compound is a cycloalkenyl iron carbonyl compound.

6. A method as in claim 5 wherein the soluble cycloalkenyl iron carbonyl compound is a cycloalkenyl iron carbonyl compound containing at least 1 cycloalkenyl ring containing from 5 to about 25 carbon atoms and from 1 to 3 carbonyl groups.

7. In a method wherein a solution of a tertiary butyl hydroperoxide charge stock in tertiary butyl alcohol that contains from about 5 to about 30 wt % of tertiary butyl hydroperoxide is brought into contact with a catalytically effective amount of a hydroperoxide decomposition catalyst in a hydroperoxide decomposition reaction zone in liquid phase with agitation under hydroperoxide conversion conditions including a temperature within the range of about 25° to about 250° C. and a pressure of about 0 to about 1,000 psig to convert said tertiary butyl hydroperoxide to decomposition products, principally tertiary butyl alcohol, the improvement which comprises:
   a) using, as said hydroperoxide decomposition catalyst, a mixture of a soluble cycloalkenyl iron compound with a soluble ruthenium compound, and
   b) recovering tertiary butyl alcohol from the products of said hydroperoxide decomposition reaction.

8. A method as in claim 7 wherein the temperature is in the range of about 40° to about 150° C., the pressure is about 0 to 50 psig, wherein the soluble alkenyl iron compound is selected from the group consisting of alkylcycloalkadienyl iron compounds and cycloalkenyl iron carbonyls and wherein the ruthenium compound consists essentially of a ruthenium salt of a mineral acid or an organic carboxylic acid.

9. A method as in claim 8 wherein the soluble iron compound is a bis(alkylcycloalkadienyl) iron compound and the soluble ruthenium compound is a salt of an organic carboxylic acid.

10. A method as in claim 9 wherein the soluble bis(alkylcycloalkadienyl) iron compound is bis(pentamethylcyclopentadienyl) iron and the soluble ruthenium compound is ruthenium acetylacetonate.

* * * * *